(12) United States Patent
Oppenheim et al.

(10) Patent No.: US 11,389,480 B2
(45) Date of Patent: Jul. 19, 2022

(54) HUMAN MONOCLONAL ANTIBODY TARGETING TNFR2 FOR CANCER IMMUNOTHERAPY

(71) Applicant: The U.S.A., as represented by the Secretary, Department of Health and Human Services, Bethesda, MD (US)

(72) Inventors: Joost J. Oppenheim, Bethesda, MD (US); Dimiter S. Dimitrov, Pittsburgh, PA (US); De Yang, Frederick, MD (US); Xin Chen, Frederick, MD (US); Zhongyu Zhu, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 385 days.

(21) Appl. No.: 16/614,652

(22) PCT Filed: May 8, 2018

(86) PCT No.: PCT/US2018/031618
§ 371 (c)(1),
(2) Date: Nov. 18, 2019

(87) PCT Pub. No.: WO2018/213064
PCT Pub. Date: Nov. 22, 2018

(65) Prior Publication Data
US 2020/0230173 A1    Jul. 23, 2020

Related U.S. Application Data

(60) Provisional application No. 62/508,827, filed on May 19, 2017.

(51) Int. Cl.
| | | |
|---|---|---|
| *A61K 39/00* | (2006.01) | |
| *A61K 35/17* | (2015.01) | |
| *A61K 47/69* | (2017.01) | |
| *A61K 47/64* | (2017.01) | |
| *A61P 35/00* | (2006.01) | |
| *C07K 16/28* | (2006.01) | |

(52) U.S. Cl.
CPC .......... *A61K 35/17* (2013.01); *A61K 47/6415* (2017.08); *A61K 47/6929* (2017.08); *A61P 35/00* (2018.01); *C07K 16/2809* (2013.01); *C07K 16/2878* (2013.01); *A61K 2039/505* (2013.01)

(58) Field of Classification Search
CPC .............................................. A61K 2039/505
See application file for complete search history.

(56) References Cited

U.S. PATENT DOCUMENTS

| 8,071,336 B2 | 12/2011 | McPherson et al. |
| 2016/0339100 A1 | 11/2016 | Harding et al. |

FOREIGN PATENT DOCUMENTS

| WO | WO 2014/085654 | 6/2014 |
| WO | WO 2014/124134 | 8/2014 |
| WO | WO 2016/187068 | 11/2016 |
| WO | WO 2017/083525 | 5/2017 |

OTHER PUBLICATIONS

Anonymous, "Biotin Anti-Mouse CD120b (TNF R Type II/p75) Antibody," In BioLegend Catalogue, Nov. 30, 2012.
Chen et al., "Targeting TNFR2, an Immune Checkpoint Stimulator and Oncoprotein, is a Promising Treatment for Cancer," *Sci. Signal.*, vol. 10:eaa12328, 2017.
Colombo et al., "Regulatory T-Cell Inhibition Versus Depletion: The Right Choice in Cancer Immunotherapy," *Nature Rev. Cancer*, vol. 7:880-887, 2007.
Harding et al., "The Immunogenicity of Humanized and Fully Human Antibodies," *mAbs*, vol. 2:256-265, 2010.
Iida et al., "Nonfucosylated Therapeutic IgG1 Antibody can Evade the Inhibitory Effect of Serum Immunoglobulin G on Antibody-Dependent Cellular Cytotoxicity through its High Binding to FcγRIIIa," *Clin Cancer Res.*, vol. 12:2879-2887, 2006.
Leclerc et al., "Control of GVHD by Regulatory T Cells Depends on TNF Produced by T Cells and TNFR2 Expressed by Regulatory T Cells," *Blood*, vol. 128:1651-1659, 2016.
Mori et al., "Non-Fucosylated Therapeutic Antibodies: The Next Generation of Therapeutic Antibodies," *Cytotechnology*, vol. 55:109-114, 2007.
Okubo et al., "Homogeneous Expansion of Human T-Regulatory Cells via Tumor Necrosis Factor Receptor 2," *Sci. Rep.*, vol. 3:3153-3163, 2013.
Peipp et al., "Antibody Fucosylation Differentially Impacts Cytotoxicity Mediated by NK and PMN Effector Cells," *Blood*, vol. 112:2390-2399, 2008.
Quast et al., "Regulation of Antibody Effector Functions through IgG Fc N-glycosylation," *Cell. Mol. Life Sci.*, vol. 74:837-847, 2017.
Torrey et al., "Targeting TNFR2 with Antagonistic Antibodies Inhibits Proliferation of Ovarian Cancer Cells and Tumor-Associated $T_{regs}$," *Sci. Signal.*, vol. 10:eaaf8608, 2017.
Van der Most et al., "Tumor Eradication After Cyclophosphamide Depends on Concurrent Depletion of Regulatory T Cells: A Role for Cycling TNFR2-Expressing Effector-Suppressor T Cells in Limiting Effective Chemotherapy," *Cancer Immunol. Immunother.*, vol. 58:1219-1228, 2009.

(Continued)

*Primary Examiner* — Stephen L Rawlings
(74) *Attorney, Agent, or Firm* — Klarquist Sparkman, LLP

(57) ABSTRACT

A human monoclonal antibody that specifically binds tumor necrosis factor receptor 2 (TNFR2), and a defucosylated form of the antibody, are described. The TNFR2-specific antibody was isolated from a human scFv phage display antibody library. The disclosed antibodies promote antibody-dependent cell-mediated cytotoxicity (ADCC) of human TNFR2$^+$ CD4$^+$ T regulatory cells in a dose- and time-dependent manner. Methods of using the TNFR2 antibodies, such as for tumor immunotherapy, are described.

41 Claims, 3 Drawing Sheets

Specification includes a Sequence Listing.

(56) References Cited

OTHER PUBLICATIONS

Vargas et al., "Fc-Optimized Anti-CD25 Depletes Tumor-Infiltrating Regulatory T Cells and Synergizes with PD-1 Blockade to Eradicate Established Tumors," *Immunity*, vol. 46:577-586, 2017.
Whiteside, "The Role of Regulatory T Cells in Cancer Immunology," ImmunoTargets and Therapy, vol. 4:159-171, 2015.
Williams et al., "Phenotypic Screening Reveals TNFR2 as a Promising Target for Cancer Immunotherapy," *Oncotarget*, vol. 7:68278-68291, 2016.
Yamane-Ohnuki et al., "Production of Therapeutic Antibodies with Controlled Fucosylation," *mAbs*, vol. 1:230-236, 2009.

HUMAN MONOCLONAL ANTIBODY TARGETING TNFR2 FOR CANCER IMMUNOTHERAPY

CROSS REFERENCE TO RELATED APPLICATIONS

This application claims the benefit of U.S. Provisional Application No. 62/508,827, filed May 19, 2017, which is herein incorporated by reference in its entirety.

FIELD

This disclosure concerns a human monoclonal antibody specific for tumor necrosis factor receptor type 2 (TNFR2) and a defucosylated form of the antibody. This disclosure further concerns use of the TNFR2-specific antibody for promoting cell death of T regulatory cells and enhancing anti-tumor immune responses.

BACKGROUND

Tumor necrosis factor receptor type 2 (TNFR2) is highly expressed by tumor-infiltrating immunosuppressive $CD4^+$ $FoxP3^+$ regulatory T cells (Tregs) and has been shown to mediate the stimulatory effect of tumor necrosis factor (TNF) on these cells. Recent studies have shown that TNFR2 plays a crucial role in stimulating the activation and proliferation of Tregs, a major checkpoint of antitumor immune responses (Chen and Oppenheim, *Sci Signal* 10:eaal2328, 2017). TNFR2 is also expressed by some types of malignant cells and the survival and growth of these tumor cells is promoted by ligands of TNFR2.

SUMMARY

Disclosed herein is a human monoclonal antibody (E4) that specifically binds TNFR2, and a defucosylated form of the antibody (E4F4). The E4 antibody was selected from a human scFv phage display library. The disclosed antibodies promote antibody-dependent cell-mediated cytotoxicity (ADCC) of human $TNFR2^+$ $CD4^+$ T regulatory cells in a dose- and time-dependent manner.

Provided herein are monoclonal antibodies, or antigen-binding fragments thereof, that bind, such as specifically bind, TNFR2. In some embodiments, the monoclonal antibodies or antigen-binding fragments include the VH domain and VL domain complementarity determining region (CDR) sequences of E4. Also provided herein are conjugates that include a disclosed monoclonal antibody, or antigen-binding fragment thereof. In some examples, provided are chimeric antigen receptors (CARs), immunoconjugates, multi-specific antibodies, antibody-drug conjugates (ADCs), antibody-nanoparticle conjugates and fusion proteins that include a monoclonal antibody or antigen-binding fragment disclosed herein. Compositions that include a TNFR2-specific monoclonal antibody or antigen-binding fragment and a pharmaceutically acceptable carrier are also provided by the present disclosure.

Also provided herein are nucleic acid molecules and vectors encoding the TNFR2-specific monoclonal antibodies, CARs, immunoconjugates, multi-specific antibodies and fusion proteins disclosed herein.

Further provided are methods of detecting expression of TNFR2 in a sample using the disclosed antibodies and antigen-binding fragments.

Also provided are methods of promoting cell death of $TNFR2^+$ $CD4^+$ T regulatory (Treg) cells by contacting the cells with a monoclonal antibody or composition disclosed herein. In some embodiments, the method is an in vitro or ex vivo method. In other embodiments, the method is an in vivo method.

Further provided herein are methods of enhancing an anti-tumor response in a subject who has a tumor by administering to the subject a TNFR2-specific monoclonal antibody or composition disclosed herein.

Also provided are methods of treating a TNFR2-positive cancer in a subject by administering to the subject a TNFR2-specific monoclonal antibody, antigen-binding fragment, CAR, isolated cell expressing a CAR, immunoconjugate, ADC, multi-specific antibody, antibody-nanoparticle conjugate, fusion protein or composition disclosed herein.

Methods of inhibiting metastasis of a TNFR2-positive cancer in a subject by administering to the subject a TNFR2-specific monoclonal antibody, antigen-binding fragment, CAR, isolated cell expressing a CAR, immunoconjugate, ADC, multi-specific antibody, antibody-nanoparticle conjugate, fusion protein or composition disclosed herein is further provided by the present disclosure.

The foregoing and other objects, features, and advantages of the invention will become more apparent from the following detailed description, which proceeds with reference to the accompanying figures.

SEQUENCE LISTING

Figure 1:
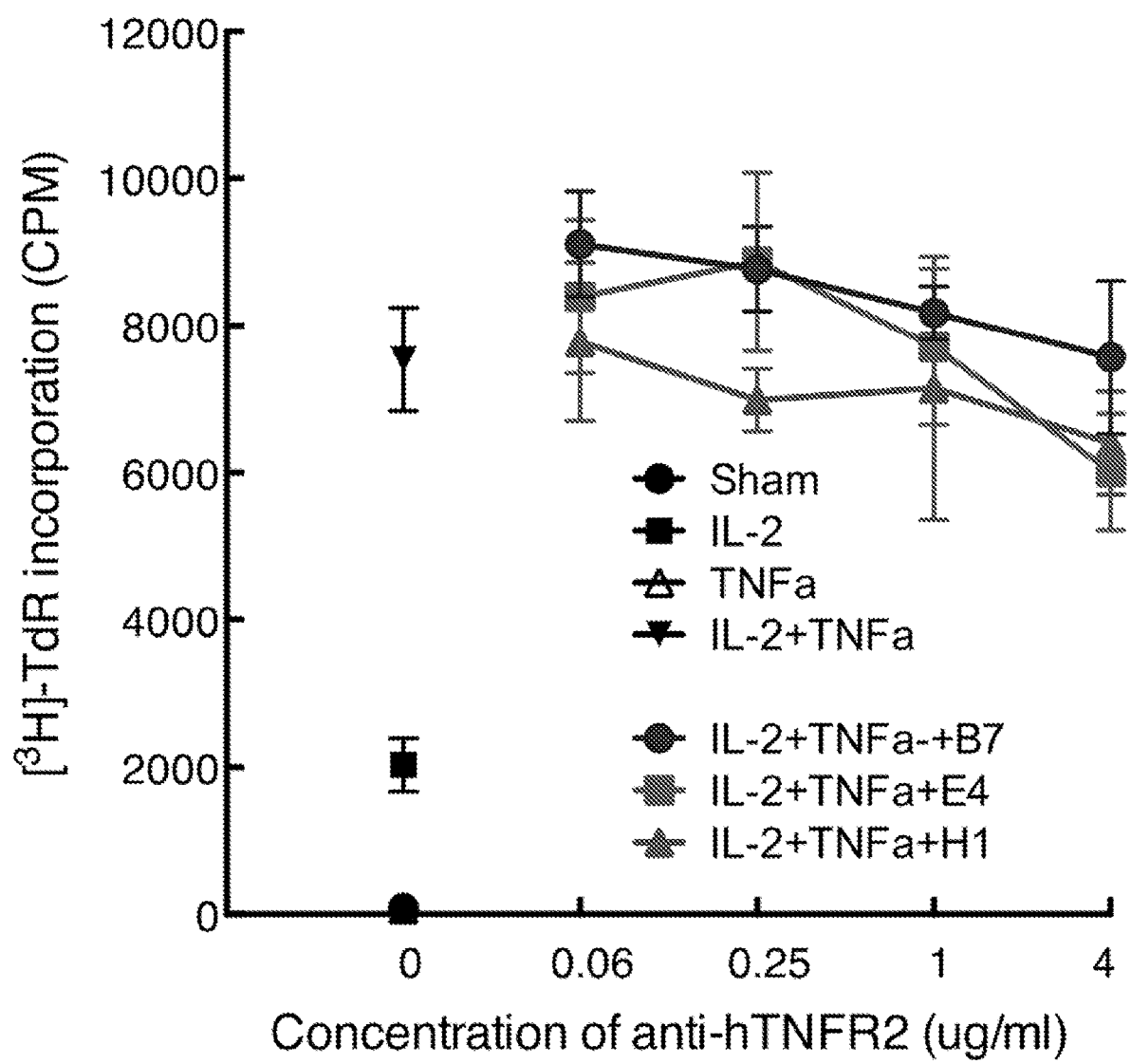
FIG. 1 is a graph showing that Treg proliferation is not inhibited by TNFR2 monoclonal antibodies B7, E4 and HI in response to TNFα.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 11, 2018, 2.48 KB, which is incorporated by reference herein. In the accompanying sequence listing:

SEQ ID NO: 1 is the amino acid sequence of the E4 VH domain.

SEQ ID NO: 2 is the amino acid sequence of the E4 VL domain.

DETAILED DESCRIPTION

I. Abbreviations

ADC antibody-drug conjugate
ADCC antibody-dependent cell-mediated cytotoxicity
CAR chimeric antigen receptor
CDR complementarity determining region
CTL cytotoxic T lymphocyte
ELISA enzyme linked immunosorbent assay
NK natural killer PE phycoerythrin
PE *Pseudomonas* exotoxin
scFv single chain variable fragment
TNF tumor necrosis factor
TNFR2 tumor necrosis factor receptor 2
Treg T regulatory
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the VL region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., JMB 273, 927-948, 1997; the "Chothia" numbering scheme), Kunik et al. (see Kunik et al., *PLoS Comput Biol* 8:e1002388, 2012; and Kunik et al., *Nucleic Acids Res* 40 (Web Server issue): W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_H H$ antibodies, and $V_L$ domain antibodies. $V_{NAR}$ antibodies are produced by cartilaginous fish, such as nurse sharks, wobbegong sharks, spiny dogfish and bamboo sharks. Camelid $V_H H$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PBDs).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as TNFR2) is an antibody that binds the antigen with high affinity and does not significantly bind other unrelated antigens.

Biological sample: A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Bispecific antibody: A recombinant protein that includes antigen-binding fragments of two different monoclonal antibodies, and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in *Harrison's Principles of Internal Medicine*, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds TNFR2 used in combination with a radioactive or chemical compound.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRI. In some instances, the endodomain further includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate is often referred to as an "immunoconjugate." When the conjugate comprises an antibody linked to a drug (e.g., a cytotoxic agent), the conjugate is often referred to as an "antibody-drug conjugate" or "ADC." Other antibody conjugates include, for example, multispecific (such as bispecific or trispecific) antibodies and chimeric antigen receptors (CARs).

Conservative variant: "Conservative" amino acid substitutions are those substitutions that do not substantially affect or decrease the affinity of a protein, such as an antibody to TNFR2. For example, a monoclonal antibody that specifically binds TNFR2 can include at most about 1, at most about 2, at most about 5, and most about 10, or at most about 15 conservative substitutions and specifically bind the TNFR2 polypeptide. The term "conservative variant" also includes the use of a substituted amino acid in place of an unsubstituted parent amino acid, provided that antibody specifically binds TNFR2. Non-conservative substitutions are those that reduce an activity or binding to TNFR2.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Defucosylated: In the context of the present disclosure, a "defucosylated" antibody refers to an antibody lacking all or substantially all fucose residues. As used herein, the term "defucosylated" is synonymous with "non-fucosylated" and "afucosylated." Human IgG1 has two N-linked biantennary complex-type oligosaccharides bound to its constant region (Fc). The oligosaccharides are composed of a trimannosyl core structure with the presence or absence of core fucose, bisecting N-acetylglucosamine (GlcNAc), galactose, and terminal sialic acid. The majority of the Fc-bound oligosaccharides are core-fucosylated. ADCC, which is triggered by lymphocyte Fcγ receptors binding to antibody Fc, is dependent upon the amount of fucose attached to the innermost GlcNAc of N-linked Fc oligosaccharide via an α-1,6-linkage (Mori et al., *Cytotechnology* 55:109-114, 2007). Therapeutic antibodies lacking core fucose have been shown to induce significantly greater ADCC compared to their fucosylated counterparts (Yamane-Ohnuki and Satoh, mAbs 1(3):230-236, 2009). Defucosylated antibodies can be generated, for example, by expression in a Chinese hamster ovary (CHO) cell line with a knockout of the α-1,6-fucosyltransferase (FUT8) enzyme, which is responsible for the core-fucosylation of Fc oligosaccharides. Specifically, FUT8 catalyzes the transfer of fucose from GDP-fucose to the innermost GlcNAc in an α-1,6-linkage (Mori et al., *Cytotechnology* 55:109-114, 2007). Other methods for antibody defucosylation include expression in host cells with reduced α-1,6 fucosylation; introduction of siRNA against the α-1,6 fucosylation relevant genes; and co-introduction of β-1,4-N-acetylglucosaminyltransferase (GnTIII) and Golgi α-mannosidase II (ManII) (see Yamane-Ohnuki and Satoh, mAbs 1(3):230-236, 2009).

Degenerate variant: In the context of the present disclosure, a "degenerate variant" refers to a polynucleotide encoding a TNFR2 polypeptide or an antibody that binds TNFR2 that includes a sequence that is degenerate as a result of the genetic code. There are 20 natural amino acids, most of which are specified by more than one codon. Therefore, all degenerate nucleotide sequences are included as long as the amino acid sequence of the TNFR2 polypeptide or antibody that binds TNFR2 encoded by the nucleotide sequence is unchanged.

Diagnostic: Identifying the presence or nature of a pathologic condition, such as cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms. Therapeutic agents (or drugs) include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to a targeting moiety, such as an anti-TNFR2 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., Pharm Ther 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as TNFR2.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

Immunoliposome: A liposome with antibodies or antibody fragments conjugated to its surface. Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PBDs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad.* Sci. U.S.A. 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_H$ of an antibody that specifically binds a TNFR2 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Tumor necrosis factor receptor 2 (TNFR2): A member of the TNF-receptor superfamily that binds tumor necrosis factor-alpha (TNFα). TNFR2 and TNFR1 form a heterocomplex that mediates the recruitment of two anti-apoptotic proteins, c-IAP1 and c-IAP2, which possess E3 ubiquitin ligase activity. TNFR2 is also known as TNFRSF1B and CD120b. Nucleotide and amino acid sequences of TNFR2 are publicly available, such as under NCBI Gene ID 7133. Exemplary mRNA and protein sequences are deposited under GenBank™ Accession Nos. NM_001066.2 and NP_001057.1, respectively.

TNFR2-positive cancer: A cancer that overexpresses TNFR2 relative to non-tumor cells. In some embodiments herein, the TNFR2-positive cancer is ovarian cancer, colon cancer, renal cell carcinoma, multiple myeloma, Hodgkin's lymphoma, or non-Hodgkin's lymphoma.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies Specific for TNFR2

TNFR2 is preferentially highly expressed on activated T regulatory cells and has a crucial role in promoting Treg proliferative expansion, phenotypical stability and in vivo immunosuppressive functions (Chen and Oppenheim, *Sci Signal* 10:eaal2328, 2017). Furthermore, the survival and growth of some tumor cells that express TNFR2 is promoted by ligands of TNFR2. Thus, the rationale for targeting TNFR2 in the treatment of tumors is two-fold—inhibitors of TNFR2 boost antitumor responses by eliminating TNFR2-expressing Tregs, and are also capable of directly killing TNFR2-expressing tumor cells.

Disclosed herein is a human TNFR2-specific monoclonal antibody, referred to as E4, which was isolated from a human scFv phage display library. Also disclosed is a defucosylated form of the antibody, referred to as E4F4. E4 and E4F4 are identical in amino acid sequence; they differ only in fucosylation. It is disclosed herein that the E4 and E4F4 antibodies promote ADCC of human TNFR2$^+$ CD4$^+$ T regulatory cells in a dose- and time-dependent manner.

TNFR2-specific antibodies can be functionally characterized as belonging to one of three different categories: (1) TNFR2 agonist, (2) TNFR2 antagonist and (3) neither TNFR2 agonist or antagonist. Characterization of antibody E4/E4F4 (see Example 1) has demonstrated that it is in the latter category—neither an antagonist nor an agonist of TNFR2. Instead, the disclosed antibody is capable of efficiently inducing ADCC of CD4+/TNFR2+ Treg cells. This efficiency is in part due to the IgG isotype of the antibody, which possesses high affinity for Fcγ receptors on NK cells, the primary cell type that mediates ADCC. In contrast, previously described TNFR2-specific antibodies are TNFR2 antagonistic antibodies. The present disclosure provides the first description of a TNFR2-specific antibody capable of inducing ADCC.

The amino acid sequences of the VH and VL domain of E4 are provided below. In the amino acid sequences below, the CDR regions are shown in bold underline and the residues of CDR1, CDR2 and CDR3 are indicated below each VH domain and VL domain sequence. One of skill in the art could readily determine the CDR boundaries using any numbering scheme, including the IMGT, Kabat or Chothia numbering schemes. For example, CDRs identified by the Kabat numbering scheme are:

E4 VH Domain
(SEQ ID NO: 1)
QITLKESGPTLVKPTQTLTLTCTFSGFSLTTSGVGVGWIRQPPGKAL

EWLALIYWDDDKRYSPSLKSRLTITKDTSKNQVVLTMTNMDPVDTAT

YYCAHLDGSGSLDYWGQGTLVTVSS

CDR1 = residues 26-35; CDR2 = residues 53-59; and

CDR3 = residues 98-108

E4 VL Domain
(SEQ ID NO: 2)
QSVLTQPPSASGTPGQRVTISCSGSTSNIGRNSVNWYSHLPGAAPKL

LISGNDQRPSGVPDRFSGSKSDNTASLTVSGLQAEDEAHYYCSSSAA

NLGVFGGGTKLTVLG

CDR1 = residues 26-33; CDR2 = residues 51-53; and

CDR3 = residues 90-98

Provided herein are isolated monoclonal antibodies, or antigen-binding fragments thereof, that bind (such as specifically bind) TNFR2. The monoclonal antibodies or antigen-binding fragments include a variable heavy (VH) domain and a variable light (VL) domain. In some embodiments, the monoclonal antibodies or antigen-binding fragments include at least a portion of the amino acid sequence set forth herein as SEQ ID NO: 1 or SEQ ID NO: 2, such as one or more (such as all three) CDR sequences from SEQ ID NO: 1 or SEQ ID NO: 2. In some examples, the CDR locations are determined IMGT, Kabat or Chothia.

In some embodiments, VH domain of the antibody (or antigen-binding fragment) comprises the CDR sequences of SEQ ID NO: 1 and the VL domain of the antibody (or antigen-binding fragment) comprises the CDR sequences of SEQ ID NO: 2. In some examples, the CDR sequences are determined using the IMGT, Kabat or Chothia numbering scheme.

In some embodiments, the VH domain of the antibody (or antigen-binding fragment) comprises residues 26-35, 53-59 and 98-108 of SEQ ID NO: 1. In some embodiments, the VL domain of the antibody (or antigen-binding fragment) comprises residues 26-33, 51-53 and 90-98 of SEQ ID NO: 2. In some examples, the VH domain of the antibody (or antigen-binding fragment) comprises residues 26-35, 53-59 and 98-108 of SEQ ID NO: 1; and the VL domain of the antibody (or antigen-binding fragment) comprises residues 26-33, 51-53 and 90-98 of SEQ ID NO: 2.

In some embodiments, the amino acid sequence of the VH domain is at least 80%, at least 85%, at least 90%, at least 95%, at least 96%, at least 97%, at least 98% or at least 99% identical to SEQ ID NO: 1 and/or the amino acid sequence of the VL domain is at least 80%, at least 85%, at least 90%, at least 95%, at least 96%, at least 97%, at least 98% or at least 99% identical to SEQ ID NO: 2.

In some embodiments, the amino acid sequence of the VH domain comprises or consists of SEQ ID NO: 1 and/or the amino acid sequence of the VL domain comprises or consists of SEQ ID NO: 2.

In some examples, antigen-binding fragment that binds TNFR2 is an Fab fragment, an Fab' fragment, an F(ab)'$_2$ fragment, a single chain variable fragment (scFv) or a disulfide stabilized variable fragment (dsFv).

In some examples, the monoclonal antibody is an IgG. In other examples, the monoclonal antibody is an IgA, IgD, IgE or IgM.

In some embodiments, the antibody or antigen-binding fragment is a fully human antibody or antigen-binding fragment. In other embodiments, the antibody or antigen-binding fragment is a chimeric, synthetic, humanized or human antibody.

Also provided herein are chimeric antigen receptors (CARs) that include a monoclonal antibody or antigen-binding fragment disclosed herein. In some embodiments, the CAR further includes a hinge region, a transmembrane domain, a costimulatory signaling moiety, a signaling domain, or any combination thereof. Further provided are cells expressing a TNFR2-specific CAR. In some examples, the cell is a T lymphocyte, such as a CTL. CARs and CAR-expressing T cells are further described in section IV.

Also provided herein are immunoconjugates that include a monoclonal antibody or antigen-binding fragment disclosed herein and an effector molecule. In some embodiments, the effector molecule is a toxin, such as, but not limited to, *Pseudomonas* exotoxin or a variant thereof. In other embodiments, the effector molecule is a detectable label, such as, but not limited to, a fluorophore, an enzyme or a radioisotope. Immunoconjugates are further described in section V.

Further provided herein are antibody-drug conjugates (ADCs) that include a drug conjugated to a monoclonal antibody or antigen-binding fragment disclosed herein. In some embodiments, the drug is a small molecule, for example an anti-microtubule agent, an anti-mitotic agent and/or a cytotoxic agent. ADCs are further described in section VI.

Also provided herein are multi-specific antibodies that include a monoclonal antibody or antigen-binding fragment disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody or antigen-binding fragment disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody or antigen-binding fragment disclosed herein and a heterologous protein or peptide. In some embodiments, the heterologous protein is an Fc protein. In some examples, the Fc protein is a mouse Fc or a human Fc protein. In some embodiments, the heterologous peptide is not endogenous to humans (for example, the heterologous peptide is a peptide neo-epitope).

Compositions that include a pharmaceutically acceptable carrier and a monoclonal antibody or antigen-binding fragment, CAR, isolated cell, immunoconjugate, ADC, multi-specific antibody, antibody-nanoparticle conjugate, or fusion protein disclosed herein are further provided by the present disclosure.

Also provided are nucleic acid molecules encoding a monoclonal antibody or antigen-binding fragment disclosed herein. Further provided are nucleic acid molecules encoding a CAR, immunoconjugate, multi-specific antibody, or fusion protein disclosed herein. In some embodiments, the nucleic acid molecule is operably linked to a promoter. Vectors that include the nucleic acid molecules are further provided herein.

IV. Chimeric Antigen Receptors (CARs)

The disclosed TNFR2 monoclonal antibodies can also be used to produce CARs. Alternatively, the disclosed TNFR2-specific monoclonal antibodies can also be used in combination with antigen-specific, such as tumor antigen-specific CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv, or is a single-domain antibody. Several different endodomains have been used to generate CARs. For example, the endodomain can consist of a signaling chain having an ITAM, such as CD3 or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, a tumor-antigen specific monoclonal antibody can be used to engineer CTLs that express a CAR containing an antigen-binding fragment of an antigen-specific antibody, thereby targeting the engineered CTLs to tumor antigen-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, T cells expressing CARs that include a TNFR2 antibody or antigen-binding fragment, can be used to directly target TNFR2-expressin tumors. Alternatively, the TNFR2 antibodies disclosed herein (which promote anti-tumor responses by killing Treg cells) can be used in combination with CARs that include a tumor antigen-specific monoclonal antibody, or antigen-binding fragment thereof, such as a scFv. In some embodiments, the CAR is a bispecific CAR.

V. Immunoconjugates

The disclosed TNFR2 monoclonal antibodies can be conjugated to a therapeutic agent or effector molecule. Alternatively, the disclosed TNFR2 antibodies can be used in combination with a tumor antigen-specific monoclonal antibody conjugated to a therapeutic agent or effector molecule (thereby producing an immunoconjugate). Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies or antibody fragments can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker, for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, J3-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with a monoclonal antibody to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is Pseudomonas exotoxin (PE) (U.S. Pat. No. 5,602,095). As used herein "*Pseudomonas exotoxin*" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with a monoclonal antibody can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022).

In other examples, the PE variant is PE with reducing immunogenicity. In yet other examples, the PE is a variant designated PE-LR/8M (PCT Publication No. WO 2011/032022). Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

Antibodies can also be used to target any number of different diagnostic or therapeutic compounds to cells expressing the tumor antigen on their surface. Thus, an antibody can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

ADCs are compounds comprised of an antigen-specific, such as a tumor antigen-specific, antibody (or antigen-binding fragment thereof) and a drug, typically a cytotoxic agent, such as an anti-microtubule agent or cross-linking agent. Because ADCs are capable of specifically targeting particular cell types, such as cancer cells, the drug can be much more potent than agents used for standard chemotherapy. The most common cytotoxic drugs currently used with ADCs have an ICso that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PBDs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

In some embodiments, the ADC is comprised of a TNFR2-specific antibody disclosed herein conjugated to a drug to specifically target TNFR2-positive tumors. In other embodiments, the TNFR2-specific antibodies and conjugates disclosed herein can be used in combination with an ADC specific for a different tumor antigen (a tumor antigen other than TNFR2). In some embodiments, the ADC includes a drug (such as a cytotoxic agent) conjugated to a monoclonal antibody that binds (such as specifically binds) a tumor antigen. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PBD, an auristatin, a maytansinoid, dolastatin, calicheamicin, nemorubicin and its derivatives, PNU-159682, anthracycline, vinca alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PBD dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663, 149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, ao-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

VII. Multi-Specific Antibodies

Multi-specific antibodies are recombinant proteins comprised of antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The antigen-specific monoclonal antibodies disclosed herein can be used to generate multi-specific (such as bispecific or trispecific) antibodies that target both the antigen (e.g. TNFR2) and CTLs, or target both the antigen and NK cells, thereby providing a means to treat tumor antigen-expressing cancers.

Bi-specific T-cell engagers (BiTEs) are a type of bispecific monoclonal antibody that are fusions of a first single-chain variable fragment (scFv) that targets a specific antigen and a second scFv that binds T cells, such as bind CD3 on T cells. In some embodiments herein, one of the binding moieties of the BiTE (such as one of the scFv molecules) is specific for TNFR2.

Bi-specific killer cell engagers (BiKEs) are a type of bispecific monoclonal antibody that are fusions of a first scFv that targets a specific antigen and a second scFv that binds a NK cell activating receptor, such as CD16. In some embodiments herein, one of the binding moieties of the BiKE (such as one of the scFv molecules) is specific for TNFR2.

Provided herein are multi-specific, such as trispecific or bispecific, monoclonal antibodies comprising a TNFR2-specific monoclonal antibody, or antigen-binding fragment thereof. In some embodiments, the multi-specific monoclonal antibody further comprises a monoclonal antibody, or antigen-binding fragment thereof, that specifically binds a component of the T cell receptor, such as CD3. In other embodiments, the multi-specific monoclonal antibody further comprises a monoclonal antibody, or antigen-binding fragment thereof, that specifically binds a NK cell activating receptor, such as CD16, Ly49, or CD94. In yet other embodiments, the multi-specific monoclonal antibody further comprises a monoclonal antibody, or antigen-binding fragment thereof, that specifically binds a tumor antigen. In some examples, the antigen-binding fragments are scFv. Also provided are isolated nucleic acid molecules and vectors encoding the multi-specific antibodies, and host cells comprising the nucleic acid molecules or vectors.

VII. Antibody-Nanoparticle Conjugates

The disclosed TNFR2-specific monoclonal antibodies, or antigen-binding fragments thereof, can be conjugated to a variety of different types of nanoparticles to deliver cytotoxic agents or other anti-cancer agents directly to tumor cells via binding of the antibody to TNFR2 expressed on the surface of tumor cells. In other embodiments, the disclosed TNFR2-specific antibodies are used in combination with antibody-nanoparticle conjugates that include a tumor antigen-specific monoclonal antibody, or antigen-binding fragment thereof for cancer immunotherapy.

The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine. Niosomes range from small, unilalamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies can be conjugated to a suitable nanoparticle according to standard methods known in the art. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Compositions and Methods of Use

Compositions are provided that include one or more of the disclosed antibodies that bind (for example specifically bind) TNFR2 in a carrier. Compositions comprising CARs (and T lymphocytes comprising CARs), ADCs, multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, CAR, ADC, CAR-expressing T lymphocyte, multi-specific antibody, antibody-nanoparticle conjugate, immunoliposome or immunoconjugate can be formulated for systemic or local administration. In one example, the antibody is formulated for parenteral administration, such as intravenous administration.

The compositions for administration can include a solution of the antibody, antigen-binding fragment, ADC, CAR, CAR-expressing T lymphocyte, multi-specific (such as bispecific or trispecific) antibody, antibody-nanoparticle conjugate, immunoliposome and/or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, ADCs, CARs, CAR-expressing T lymphocytes, multi-specific (such as bispecific or trispecific) antibodies, antibody-nanoparticle conjugates, immunoliposomes and/or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems,* Technomic Publishing Company, Inc., Lancaster, Pa., (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems,* J. Kreuter, ed., Marcel Dekker, Inc., New York, N.Y., pp. 219-342 (1994); and Tice & Tabibi, *Treatise on Controlled Drug Delivery,* A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems,* Technomic Publishing Co., Inc., Lancaster, Pa. (1993)). Numerous additional systems for controlled delivery of therapeutic proteins are known (see U.S. Pat. Nos. 5,055,303; 5,188,837; 4,235, 871; 4,501,728; 4,837,028; 4,957,735; 5,019,369; 5,055, 303; 5,514,670; 5,413,797; 5,268,164; 5,004,697; 4,902,505; 5,506,206; 5,271,961; 5,254,342 and 5,534,496).

A. Therapeutic Methods

The antibodies and compositions disclosed herein can be administered to slow or inhibit the growth of tumor cells, to inhibit the metastasis of tumor cells and/or to enhance an anti-tumor immune response. In these applications, a therapeutically effective amount of a composition is administered to a subject in an amount sufficient to inhibit growth, replication or metastasis of cancer cells, to inhibit a sign or a symptom of the cancer, and/or to increase an immune response against the cancer.

Provided herein is a method of enhancing an anti-tumor immune response in a subject who has a tumor/cancer by administering to the subject a TNFR2-specific monoclonal antibody (or antigen-binding fragment thereof) disclosed herein, or a composition disclosed herein. Also provided is a method of treating a TNFR2-positive cancer in a subject by administering to the subject a TNFR2-specific monoclonal antibody, antigen-binding fragment, CAR, isolated cell expressing a CAR, immunoconjugate, ADC, multi-specific antibody, antibody-nanoparticle conjugate, fusion protein or composition disclosed herein. Further provided is a method of inhibiting metastasis of a TNFR2-positive cancer in a subject by administering to the subject a TNFR2-specific monoclonal antibody, antigen-binding fragment, CAR, isolated cell expressing a CAR, immunoconjugate, ADC, multi-specific antibody, antibody-nanoparticle conjugate, fusion protein or composition disclosed herein.

Also provided herein are methods of promoting cell death of $TNFR2^+ CD4^+$ T regulatory (Treg) cells by contacting the cells with a monoclonal antibody or composition disclosed herein. In some embodiments, the method is an in vitro or ex vivo method. In other embodiments, the method is an in vivo method.

A therapeutically effective amount of a TNFR2-specific antibody or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the antibodies, antibody conjugates and compositions disclosed herein can also be accompanied by administration of other anti-cancer agents or therapeutic treatments (such as surgical resection of a tumor). In some embodiments, the TNFR2-specific antibody, antibody conjugate or composition is administered in combination with radiotherapy, chemotherapy, an ADC, an immunotoxin, a CAR-expressing T cell, or an immune checkpoint targeted therapy, such as anti-cytotoxic T-lymphocyte-associated protein 4 (CTLA-4) antibody, anti-OX40 antibody, anti-glucocorticoid-induced TNF receptor-related (GITR) antibody, anti-inducible co-stimulator (ICOS) antibody, anti-lymphocyte activation gene 3 (LAG3) antibody, anti-T-cell immunoglobulin domain and mucin domain 3 (TIM3) antibody, anti-CD276 (B7-H3) antibody, or an indoleamine 2,3-dioxygenase (IDO) inhibitor.

Any suitable anti-cancer agent can be administered in combination with the antibodies, compositions and conjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran™, Ara-C, BiCNU, Busulfan, CCNU, Carboplatinum, Cisplatinum, Cytoxan™, Daunorubicin, DTIC, 5-FU, Fludarabine, Hydrea™, Idarubicin, Ifosfamide, Methotrexate, Mithramycin, Mitomycin, Mitoxantrone, Nitrogen Mustard, Taxol™ (or other taxanes, such as docetaxel), Velban, Vincristine, VP-16, while some more newer drugs include Gemcitabine (Gemzar™), Herceptin™, Irinotecan (Camptosar, CPT-11), Leustatin, Navelbine™, Rituxan™, STI-571, Taxotere™, Topotecan (Hycamtin™), Xeloda™ (Capecitabine), Zevelin™ and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting TNFR2 protein in vitro or in vivo. In some cases, TNFR2 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of detecting expression of TNFR2 in a sample. In some embodiments, the method includes contacting the sample with a TNFR2-specific monoclonal antibody or antigen-binding fragment disclosed herein, and detecting binding of the antibody to the sample. In some examples, the sample is a blood, cell or tissue sample.

Also provided herein is a method of determining if a subject has a TNFR2-positive cancer by contacting a sample from the subject with a TNFR2-specific monoclonal antibody disclosed herein; and detecting binding of the antibody to the sample. An increase in binding of the antibody to the sample as compared to binding of the antibody to a control sample identifies the subject as having a TNFR2-positive cancer.

In another embodiment, provided is a method of confirming a diagnosis of a TNFR2-positive cancer in a subject by contacting a sample from a subject diagnosed with a TNFR2-positive cancer with a TNFR2-specific monoclonal antibody disclosed herein; and detecting binding of the antibody to the sample. An increase in binding of the antibody to the sample as compared to binding of the antibody to a control sample confirms the diagnosis of a TNFR2-positive cancer in the subject.

In some examples of the disclosed methods, the monoclonal antibody is directly labeled. In other examples, the methods further include contacting a second antibody that specifically binds the monoclonal antibody with the sample; and detecting the binding of the second antibody. An increase in binding of the second antibody to the sample as compared to binding of the second antibody to a control sample detects expression of TNFR2 expression in the sample. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, TNFR2 protein can be assayed in a biological sample by a competition immunoassay utilizing TNFR2 protein standards labeled with a detectable substance and an unlabeled antibody that specifically binds TNFR2. In this assay, the biological sample, the labeled TNFR2 protein standards and the antibody that specifically binds TNFR2 are combined and the amount of labeled TNFR2 protein standard bound to the unlabeled antibody is determined. The amount of TNFR2 in the biological sample is inversely proportional to the amount of labeled TNFR2 protein standard bound to the antibody that specifically binds TNFR2.

The immunoassays and methods disclosed herein can be used for a number of purposes. In one embodiment, the antibody that specifically binds TNFR2 may be used to detect the production of TNFR2 in cells in cell culture. In another embodiment, the antibody can be used to detect the amount of TNFR2 in a biological sample, such as a tissue sample, or a blood or serum sample. In some examples, the TNFR2 is cell-surface TNFR2. In other examples, the TNFR2 is soluble (e.g. in a cell culture supernatant or in a body fluid sample, such as a blood or serum sample).

In one embodiment, a kit is provided for detecting TNFR2 in a biological sample, such as a blood sample or tissue sample. Kits for detecting a polypeptide will typically include a monoclonal antibody that specifically binds TNFR2, such as TNFR2 antibody disclosed herein. In a further embodiment, the antibody is labeled (for example, with a fluorescent, radioactive, or an enzymatic label).

In one embodiment, a kit includes instructional materials disclosing means of use of an antibody that binds TNFR2. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting TNFR2 in a biological sample generally includes the steps of contacting the biological sample with an antibody which specifically reacts, under immunologically reactive conditions, to TNFR2. The antibody is allowed to specifically bind under immunologically reactive conditions to form an immune complex, and the presence of the immune complex (bound antibody) is detected directly or indirectly.

The antibodies disclosed herein can also be utilized in immunoassays such as but not limited to radioimmunoassays (RIAs), ELISA, Western blot, immunoprecipitation assays or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620).

The following examples are provided to illustrate certain particular features and/or embodiments. These examples should not be construed to limit the disclosure to the particular features or embodiments described.

EXAMPLES

Example 1: Isolation and Characterization of TNFR2-Specific Antibodies

Three human TNFR2-specific antibodies (B7, E4 and HI) were generated by screening a phage display scFv library using human TNFR2-Fc fusion protein as target (Puri et al.,

*mAbs* 5: 533-539, 2013). First, the antibodies were tested for their in vitro capacity to inhibit the TNFα-induced proliferative response of human Tregs. Human TNFR2 is predominantly expressed by Treg CD4+ T cells and TNFα can promote Treg expansion in the presence of human IL-2. Therefore, the activity of anti-human TNFR2 antibodies was tested by determining their effects on TNFα-induced expansion of Treg (by interacting with TNFR2). Purified human peripheral blood CD4+ T cells were purified and cultured for three days in the presence or absence of human IL-2, human TNFα or anti-TNFR2 antibody, alone or in combination. Treg proliferation was measured by [$^3$H]-TdR incorporation and the number of CD4+CD25$^h$ Tregs was determined by flow cytometry. The results demonstrated that none of the three antibodies significantly inhibited Treg proliferation (FIG. 1). The three antibodies also did not show any agonistic activity.

Figure 2:
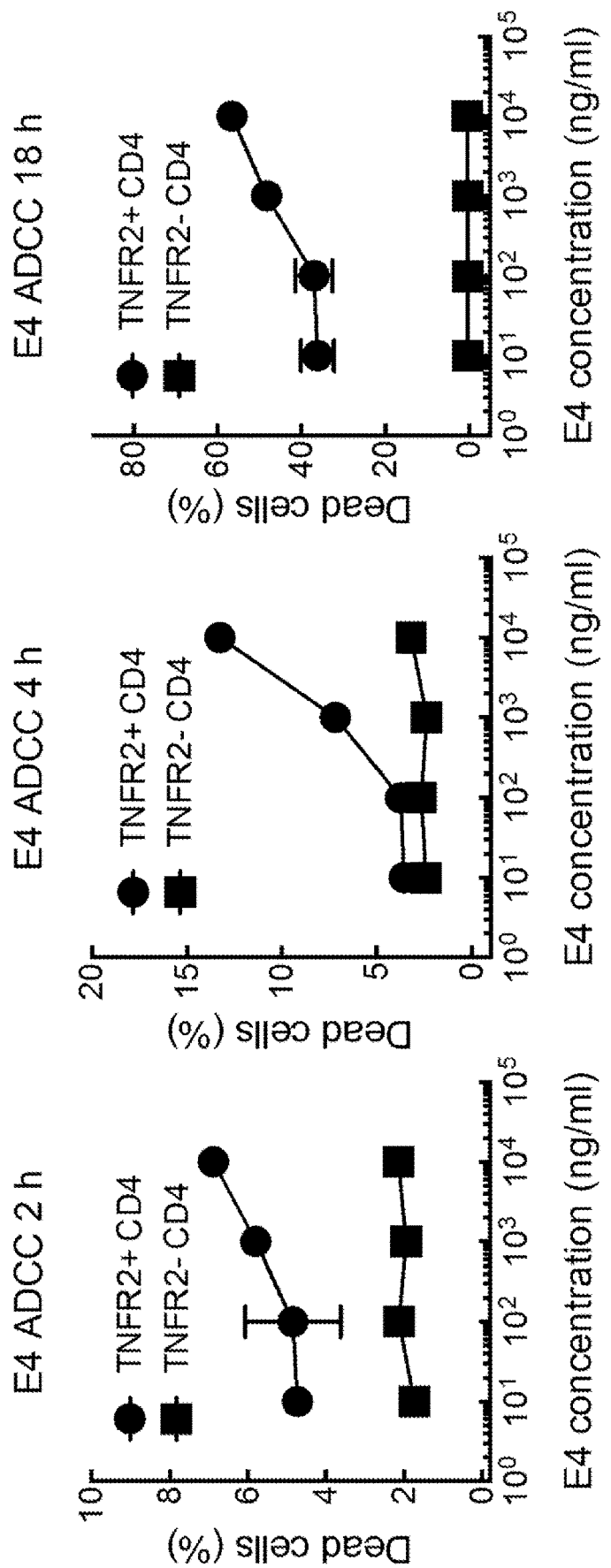
FIG. 2 is a series of graphs demonstrating the ADCC effect of antibody E4.

Antibody E4 was then tested for the capacity to mediate antibody-dependent cell cytotoxicity (ADCC). The ADCC effect of E4 was tested at an effector (NK cell) to target (CD4 T cell) ratio of 10:1 using an antibody concentration range of 0 to about 10,000 ng/ml. The results indicated that E4 mediated ADCC of human TNFR2-positive CD4+ T regulatory cells in a dose- and time-dependent manner (FIG. 2). Furthermore, E4 was not cytotoxic for human TNFR2− CD4+ cells.

Figure 3:
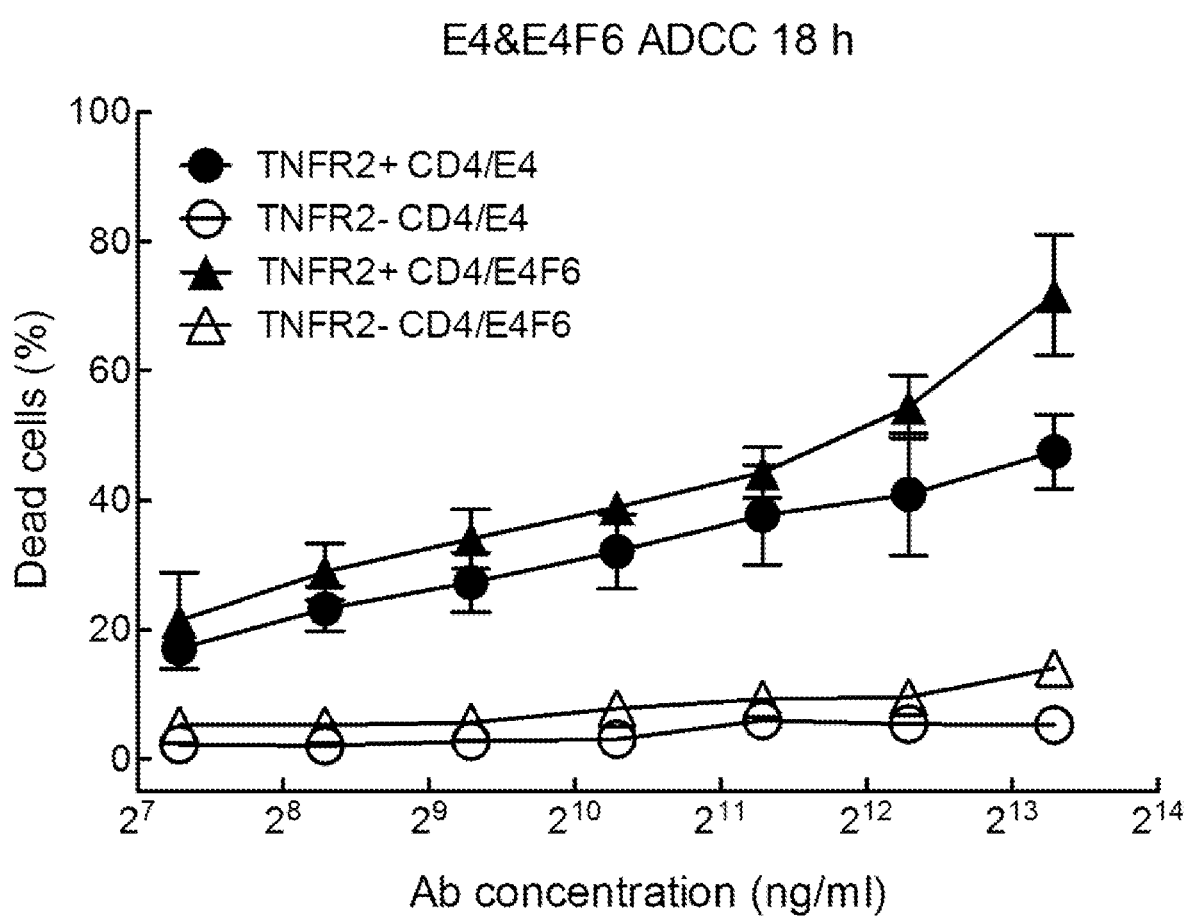
FIG. 3 is a graph showing ADCC of human donor CD4+ T cells following incubation with antibody E4 or E4F6. Data are shown as the average (mean±SD) of 5 donors.

To further enhance its ADCC activity, E4 was defucosylated (Iida et al., *Clin Cancer Res* 12(9):2879-2887, 2006). The capacity of defucosylated antibody (E4F6) to mediate ADCC killing of human CD4+ T cells was then compared with E4. The experiments were carried out in triplicate using 96-well plates at a total volume of 0.2 ml/well. CD4+ T cells (40,000/well) were incubated with E4 or E4F4 at various doses (156, 312, 625, 1250, 5000, and 10,000 ng/ml) in RPMI 1640 medium for 20 minutes before the addition of NK cells (400,000/well). Normal human IgG at 10,000 ng/ml was used as a negative control. For the positive control wells, NaN$_3$ was added to a final concentration of 0.25%. After incubation for 18 hours, the cells were immunostained with FITC-AxV/P.I., PE-Cy7-anti-hTNFR2, and Pacific Blue-anti-hCD4. Subsequently, the cells were analyzed using a LSRII flow cytometer and the data were collected (200,000 cells/sample). The data were analyzed using FlowJo. The ADCC effect was tested at an effector (NK) to target (CD4) ratio of 10:1 using a concentration range of 156 to about 10,000 ng/ml. Data in FIG. 3 are shown as the average of 5 donors.

The results indicated that both E4 and E4F6 mediated ADCC of human TNFR2+CD4 T cells in a dose-dependent manner, and that E4F6 was more effective than E4 at inducing ADCC. In particular, E4F6 exhibited up to about 80% killing of the TNFR2+ CD4 Treg cells at the highest concentration used (FIG. 3).

Example 2: Induction of ADCC In Vivo

This example describes a study to evaluate the capacity of E4 and E4F6 to induce ADCC of human CD4+/TNFR2+ T regulatory cells in an animal model.

Antibody E4/E4F4 does not recognize mouse TNFR2. Therefore, to evaluate the functional effect of the TNFR2 antibody in vivo, the antibody is tested in immunodeficient (nude) mice that have been re-populated with human CD4+ T cells and human NK cells. The mice are administered E4, E4F6 or a control IgG1 antibody and the number of CD4+/TNFR2+ T regulatory cells before and after antibody administration are determined. It is expected that administration of E4 and E4F6 will result in a decrease in CD4+/TNFR2+ Tregs compared with control IgG1 treated mice.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. A monoclonal antibody that binds tumor necrosis factor receptor 2 (TNFR2), or an antigen-binding fragment thereof, comprising a variable heavy (VH) domain and a variable light (VL) domain, wherein:
   the VH domain comprises the complementarity determining region (CDR) sequences of SEQ ID NO: 1; and
   the VL domain comprises the CDR sequences of SEQ ID NO: 2.

2. The monoclonal antibody or antigen-binding fragment of claim 1, wherein the CDR sequences are determined using the IMGT, Kabat or Chothia numbering scheme.

3. The monoclonal antibody or antigen-binding fragment of claim 1, wherein:
   the VH domain comprises residues 26-35, 53-59 and 98-108 of SEQ ID NO: 1; and
   the VL domain comprises residues 26-33, 51-53 and 90-98 of SEQ ID NO: 2.

4. The monoclonal antibody or antigen-binding fragment of claim 1, wherein:
   the amino acid sequence of the VH domain is at least 90% identical to SEQ ID NO: 1; and
   the amino acid sequence of the VL domain is at least 90% identical to SEQ ID NO: 2.

5. The monoclonal antibody or antigen-binding fragment of claim 1, wherein:
   the amino acid sequence of the VH domain comprises SEQ ID NO: 1; and
   the amino acid sequence of the VL domain comprises SEQ ID NO: 2.

6. The antigen-binding fragment of claim 1, wherein the antigen-binding fragment is an Fab fragment, an Fab' fragment, an F(ab)'$_2$ fragment, a single chain variable fragment (scFv) or a disulfide stabilized variable fragment (dsFv).

7. The monoclonal antibody of claim 1, wherein the antibody is an IgG.

8. The monoclonal antibody or antigen-binding fragment of claim 1, which is a fully human antibody or antigen-binding fragment.

9. The monoclonal antibody or antigen-binding fragment of claim 1, which is a chimeric or synthetic antibody or antigen-binding fragment.

10. The monoclonal antibody of claim 1, wherein the antibody is defucosylated.

11. An immunoconjugate comprising the monoclonal antibody or antigen-binding fragment of claim 1 and an effector molecule.

12. The immunoconjugate of claim 11, wherein the effector molecule is a toxin.

13. The immunoconjugate of claim 12, wherein the toxin is *Pseudomonas* exotoxin or a variant thereof.

14. The immunoconjugate of claim 11, wherein the effector molecule is a detectable label.

15. The immunoconjugate of claim 14, wherein the detectable label comprises a fluorophore, an enzyme or a radioisotope.

16. An antibody-drug conjugate (ADC) comprising a drug conjugated to the monoclonal antibody or antigen-binding fragment of claim 1.

17. The ADC of claim 16, wherein the drug is a small molecule.

18. The ADC of claim 16, wherein the drug is an anti-microtubule agent, an anti-mitotic agent and/or a cytotoxic agent.

19. A multi-specific antibody comprising the monoclonal antibody or antigen-binding fragment of claim 1 and at least one additional monoclonal antibody or antigen-binding fragment thereof.

20. The multi-specific antibody of claim 19, which is a bispecific antibody.

21. The multi-specific antibody of claim 19, which is a trispecific antibody.

22. The multi-specific antibody of claim 19, wherein the at least one additional monoclonal antibody or antigen binding fragment thereof specifically binds a component of the T cell receptor or a natural killer (NK) cell activating receptor.

23. An antibody-nanoparticle conjugate, comprising a nanoparticle conjugated to the monoclonal antibody or antigen-binding fragment of claim 1.

24. The antibody-nanoparticle conjugate of claim 23, wherein the nanoparticle comprises a polymeric nanoparticle, nanosphere, nanocapsule, liposome, dendrimer, polymeric micelle, or niosome.

25. The antibody-nanoparticle conjugate of claim 23, wherein the nanoparticle comprises a cytotoxic agent.

26. A fusion protein comprising the monoclonal antibody or antigen-binding fragment of claim 1 and a heterologous protein or peptide.

27. The fusion protein of claim 26, wherein the heterologous protein is an Fc protein.

28. A composition comprising a pharmaceutically acceptable carrier and the monoclonal antibody or antigen-binding fragment of claim 1.

29. A nucleic acid molecule encoding the monoclonal antibody or antigen-binding fragment of claim 1.

30. The nucleic acid molecule of claim 29, operably linked to a promoter.

31. A vector comprising the nucleic acid molecule of claim 29.

32. A method of detecting expression of TNFR2 in a sample, comprising:
   contacting the sample with the monoclonal antibody or antigen-binding fragment of claim 1; and
   detecting binding of the antibody to the sample, thereby detecting expression of TNFR2 in the sample.

33. The method of claim 32, wherein the monoclonal antibody or antigen-binding fragment is directly labeled.

34. The method of claim 32, further comprising:
   contacting the monoclonal antibody or antigen-binding fragment with a second antibody, and
   detecting the binding of the second antibody to the monoclonal antibody or antigen-binding fragment, thereby detecting expression of TNFR2 in the sample.

35. A method of promoting cell death of $TNFR2^+$ $CD4^+$ T regulatory (Treg) cells, comprising contacting the cells with the monoclonal antibody of claim 1.

36. The method of claim 35, which is an in vitro or ex vivo method.

37. The method of claim 35, which is an in vivo method wherein contacting the cells with the monoclonal antibody comprises administering the monoclonal antibody to a subject who has a tumor.

38. A method of enhancing an anti-tumor response in a subject who has a tumor, comprising administering to the subject the monoclonal antibody of claim 1.

39. A method of treating a TNFR2-positive cancer in a subject, comprising administering to the subject the monoclonal antibody or antigen-binding fragment of claim 1, thereby treating the TNFR2-positive cancer.

40. A method of inhibiting metastasis of a TNFR2-positive cancer in a subject, comprising administering to the subject the monoclonal antibody or antigen-binding fragment of claim 1, thereby inhibiting metastasis of the TNFR2-positive cancer.

41. The method of claim 35, wherein the antibody is defucosylated.

\* \* \* \* \*

SEQUENCE LISTING

```
<160> NUMBER OF SEQ ID NOS: 2

<210> SEQ ID NO 1
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95
```

```
Cys Ala His Leu Asp Gly Ser Gly Ser Leu Asp Tyr Trp Gly Gln Gly
            100                 105                 110

Thr Leu Val Thr Val Ser Ser
        115

<210> SEQ ID NO 2
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Arg Asn
            20                  25                  30

Ser Val Asn Trp Tyr Ser His Leu Pro Gly Ala Ala Pro Lys Leu Leu
        35                  40                  45

Ile Ser Gly Asn Asp Gln Arg Pro Ser Gly Val Pro Asp Arg Phe Ser
    50                  55                  60

Gly Ser Lys Ser Asp Asn Thr Ala Ser Leu Thr Val Ser Gly Leu Gln
65                  70                  75                  80

Ala Glu Asp Glu Ala His Tyr Tyr Cys Ser Ser Ser Ala Ala Asn Leu
                85                  90                  95

Gly Val Phe Gly Gly Gly Thr Lys Leu Thr Val Leu Gly
            100                 105
```